United States Patent [19]

Packett

[11] Patent Number: 5,243,099
[45] Date of Patent: Sep. 7, 1993

[54] SYNTHESIS OF ALPHA-SUBSTITUTED ALKADIENES

[75] Inventor: Diane L. Packett, South Charleston, W. Va.

[73] Assignee: Union Carbide Chemicals & Plastics Technology Corporation, Danbury, Conn.

[21] Appl. No.: 942,401

[22] Filed: Sep. 9, 1992

Related U.S. Application Data

[62] Division of Ser. No. 803,229, Dec. 6, 1991, Pat. No. 5,169,981.

[51] Int. Cl.$^5$ .................. C07C 29/36; C07C 33/02; C07C 67/47; C07C 69/007
[52] U.S. Cl. ........................ 568/909.5; 546/352; 556/461; 560/225; 560/261; 562/95; 562/113; 564/408; 564/485; 568/626; 568/630; 568/690
[58] Field of Search ................ 568/909.5, 690, 626, 568/630; 560/225, 261; 562/113, 95; 564/408, 485; 546/352; 556/461

[56] References Cited

U.S. PATENT DOCUMENTS

| | | | |
|---|---|---|---|
| 3,407,224 | 10/1968 | Smutny | 508/909.5 |
| 3,530,187 | 9/1970 | Shryn1 | 508/690 |
| 3,534,088 | 10/1970 | Bryant et al. | 260/497 |
| 3,670,032 | 6/1972 | Romanelli | 508/909.5 |
| 3,711,534 | 1/1973 | Manyik et al. | 260/475 |
| 3,769,352 | 10/1973 | Romanelli | 508/690 |
| 3,992,456 | 11/1976 | Atkins et al. | 260/632 |
| 4,142,060 | 2/1979 | Kuntz | 568/840 |
| 4,146,738 | 3/1979 | Jadamus et al. | 508/690 |
| 4,417,079 | 11/1983 | Yoshimura et al. | 568/903 |
| 4,774,361 | 9/1988 | Maher et al. | 568/454 |
| 4,831,183 | 5/1989 | Hanes | 508/630 |
| 4,962,243 | 10/1990 | Roeper et al. | 508/909.5 |
| 4,990,698 | 2/1991 | Wada et al. | 508/909.5 |
| 5,043,487 | 8/1991 | Thome et al. | 508/909.5 |
| 5,057,631 | 10/1991 | Tokitoh et al. | 508/909.5 |

FOREIGN PATENT DOCUMENTS

| | | | |
|---|---|---|---|
| 25740 | 3/1981 | European Pat. Off. | 568/909.5 |
| 0296550 | 12/1988 | European Pat. Off. | |
| 1354507 | 9/1971 | United Kingdom | 568/909.5 |
| 2107700 | 5/1983 | United Kingdom | 568/909.5 |

*Primary Examiner*—Joseph E. Evans
*Attorney, Agent, or Firm*—S. H. Hegedus

[57] ABSTRACT

Organic polymer additive containing polar functional groups enhances the stability of palladium-containing catalysts for the telomerization of conjugated diolefins in the presence of active hydrogen-containing telomerization agent to produce alpha-substituted alkadienes.

6 Claims, No Drawings

SYNTHESIS OF ALPHA-SUBSTITUTED ALKADIENES

This application is a division of prior U.S. application Ser. No. 07/803,229 filed on Dec. 6, 1991 now U.S. Pat. No. 5,169,981.

This invention relates to telomerization processes for making alpha-substituted alkadienes from conjugated olefins in the presence of telomerization agent and palladium-containing catalyst and to palladium-containing catalysts useful for such processes. More particularly, the invention relates to telomerization processes in which organic polymer additive containing polar functional groups is provided in the reaction menstruum to enhance catalyst stability. Advantageously, the processes of this invention enable recovery of substituted alkadiene product from the reaction menstruum without undue deleterious loss of catalyst and/or catalyst activity.

BACKGROUND OF THE INVENTION

Substituted alkadienes, especially alpha-substituted alkadienes, such as octadien-1-ol have numerous utilities including as chemical intermediates to make alcohols and esters useful in the electroplating, plastics, perfume and pharmaceutical industries and as microbials. Considerable efforts have been expended by numerous researchers to develop cost advantaged processes for the synthesis of alpha-substituted alkadienes, e.g., octadien-1-ol.

A much suggested synthesis of alkadienes involves the telomerization of conjugated diene in the presence of water and homogeneous palladium-containing catalyst. See, for instance, U.S. Pat. Nos. 3,534,088 and 3,711,534. Palladium catalyst, however, is expensive and workers in the field have thus devoted considerable efforts to reduce the amount of palladium required and/or improve recovery of active, homogeneous catalyst from the alkadiene product in order to achieve commercial viability. Particular attention has been devoted toward a. increasing the activity of the palladium catalyst to minimize the concentration of palladium in the reaction menstruum, b. enhancing selectivity to synthesize alkadien-1-ol, c maintaining the activity of the catalyst to avoid frequent catalyst regeneration procedures, d. reducing temperature sensitivity of the catalyst, and e. efficiently recovering the catalyst from the products for recycle without unduly adverse effect on its catalytic properties.

A particularly troublesome problem has been to obtain a catalyst which excels in activity, selectivity, efficiency of recovery and stability. For instance, the use of phosphine in the reaction menstruum in high ratios with respect to palladium present results in catalysts with enhanced stability but at the cost of selectivity and activity.

U.S. Pat. No. 4,774,361 discloses the use of organic polymer additive to minimize or prevent the rhodium of a rhodium organophosphite complex catalyst from precipitating from solution during a liquid recycle hydroformylation process. This patent provides no disclosure relating to the synthesis of alpha-substituted alkadienes or to palladium-containing catalysts.

SUMMARY

By this invention, palladium-containing catalysts for the telomerization of conjugated dienes to alpha-substituted alkadienes are provided which can exhibit enhanced stability and temperature tolerance, yet still can exhibit highly-desirable activity and selectivity to the alpha-substituted product. In accordance with this invention, organic polymer additive containing polar functional groups is provided in the reaction menstruum in an amount sufficient to enhance the stability of the palladium-containing telomerization catalyst. The palladium-containing catalyst comprises complex of at least one of palladium and palladium compound with phosphorus-based ligand. In the synthesis of substituted alkadienes, conjugated diolefin of four to about 8 carbon atoms is reacted under telomerization conditions including the presence of palladium-containing catalyst, organic polymer additive, active hydrogen-containing telomerization agent and substantially inert, liquid solvent for both the conjugated diolefin and the alpha-substituted alkadiene. In preferred aspects of this invention, the organic polymer additive has at least two, preferably at least three, polar functional groups, wherein the functional groups are one or more of amide, ketone, carbamate, urea and carbonate groups.

In a further aspect of the invention, the solvent for the telomerization process comprises sufficient dialkylalkylene urea solvent to reduce crystallization of a palladium and phosphorus-based ligand telomerization catalyst during catalyst separation from the reaction menstruum. Advantageous dialkylalkylene ureas enhance the selectivity of the process towards the production of alpha-substituted alkadienes.

DETAILED DISCUSSION

In the process for synthesizing alpha-substituted alkadienes, conjugated diolefin is reacted in the presence of a telomerization agent. The conjugated diolefin typically comprises 4 to about 8 carbon atoms. The conjugated diolefins may be represented by the structural formula

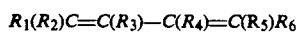

$$R_1(R_2)C=C(R_3)-C(R_4)=C(R_5)R_6$$

wherein $R_1$, $R_2$, $R_3$, $R_4$, $R_5$ and $R_6$ may be the same or different and may be hydrogen or hydrocarbyl of 1 to about 10 carbon atoms. Preferably, each of $R_2$, $R_3$, and $R_5$ are hydrogen, and more preferably, at least one of $R_1$, $R_4$, and $R_6$ are hydrogen and any of $R_1$, $R_4$, and $R_6$ that are other than hydrogen are lower alkyl, e.g., methyl, ethyl or propyl. For purposes herein, the first carbon forming the first olefinic bond of the diolefin is referred to herein as the alpha carbon, regardless of whether it is substituted with a further hydrocarbyl-containing group. Illustrative of conjugated diolefins are butadiene, isoprene, piperylene, and dimethylbutadiene. Since conjugated diolefins, e.g., butadiene, are generally readily available in unrefined process streams, the ability of the processes of this invention to use such crude streams can enhance commercial attractiveness. In some instances, removal of acetylenic components is desirable.

The telomerization agent comprises compound having at least one active hydrogen atom, and may be structurally represented by $HR_7$. Thus, telomerization agents include water, alcohols, phenols, acids, amines, silanols and reactive methylene compounds. To directly produce alkadienols, water is the preferred telomerization agent. Other compounds containing active hydrogen atom are exemplified by methanol, isopropanol, tertiary butanol, allyl alcohol, benzyl alcohol, phenol, cresol, benzoic acid, phthalic acid, propionic acid, acrylic acid, acetic acid, crotonic acid, ammonia, aniline, piperidine, diethylamine, benzoylacetone and nitromethane.

The alpha-substituted alkadiene product may be represented by the formula

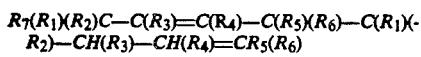

or

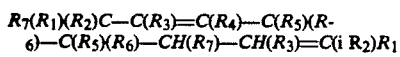

wherein $R_7$ is the residue of the telomerization agent. With water, $R_7$ is —OH, and with alcohols and phenols, $R_7$ is —OR, wherein R is often hydrocarbyl of 1 to about 20, preferably 1 to 8 carbon atoms. Thus, by selection of the telomerization agent, desirable functional groups may be provided on the synthesized molecule. The reaction can also produce a compound in which the residue of the telomerization agent is on an internal carbon atom.

The catalyst for the telomerization comprises palladium complexed with phosphorus-based ligand. Although benefits provided by this invention may be obtained in heterogeneous systems, the processes are virtually always conducted as homogeneous liquid phase reactions and thus the ultimate catalytic species are soluble in a liquid phase of the reaction menstruum. The catalyst is typically derived from a palladium compound which, for the convenience of preparation, may be soluble in a liquid phase of the reaction menstruum. Illustrative palladium compounds are set forth at column 3, lines 1 to 44, of U.S. Pat. No. 3,711,534; column 3, lines 12 to 62, of U.S. Pat. No. 3,992,456, and column 4, line 65, to column 5, line 20, of U.S. Pat. No. 4,142,060, all herein incorporated by reference. Palladium (II) acetylacetonate is conveniently used.

The catalyst also contains phosphorus-based ligand. The ligand can improve catalyst performance. Exemplary of phosphorus-based ligand are those from trihydrocarbyl phosphines, trihydrocarbyl phosphites, mono- and di-(alkoxy) phenyl phosphines, bicyclophosphites and biphosphites. See column 4, line 18, to column 5, line 20, of U. S. Pat. No. 3,992,456; column 3, line 21, to column 7, line 30, of U.S. Pat. No. 4,417,079; and column 2, line 27, to column 3, line 3, and column 4, lines 11 to 49, of U.S. Pat. No. 4,142,060, all of which are hereby incorporated by reference. Another class of ligand is derived from phosphonium salts such as disclosed in European Patent Application 296,550, herein incorporated by reference. Most frequently, trisubstituted phosphines having as substituents aryl and alkyl groups, e.g., of 1 to 10 carbons for alkyl groups, and 6 to about 12 carbons for aryl groups, are used such as tri-n-octylphosphine, tributylphosphine, dimethyl-n-octylphosphine, tricyclohexylphosphine, triphenylphosphine, and dimethylphenylphosphine. When bidentate ligands are used, e.g., bis(diphenylphosphino)methane, the ligand, for purposes of calculating the atomic ratio of phosphorus to palladium, is considered to have two phosphorus atoms.

Other ligands useful with palladium-containing catalysts for the synthesis of substituted alkadienes include nitrogen-based ligands such as derived from bidentate nitrogen-containing compounds, imides, tertiary amines, cyclic amines, aliphatic diamines, cyclic diamines and polyamines, and isonitriles. Sometimes, these ligands have no material affect on the catalytic properties of the palladium-containing catalyst but serve as additional protection against the deposition of palladium during the course of the reaction. Some of the ligands, e.g., tertiary amines and isonitriles, may enhance catalytic properties. See, for instance, U.S. Pat. No. 3,992,456, column 6, line 27, to column 7, line 2, and U.S. Pat. No. 4,417,079, column 7, lines 30 to 58; both herein incorporated by reference.

The complex of the palladium and the phosphorus-based ligand, and optionally the nitrogen-based ligand, can be prepared separately or generated in situ in the reaction menstruum. When prepared separately, the complex may conveniently be prepared in solution in a liquid to be added to the reaction menstruum. Moderate temperatures can be used to prepare the complex, e.g., between about 20° and 120° C. Advantageously, the catalyst is maintained in an atmosphere relatively devoid of reactive oxygen to prevent oxidation of the phosphorus-based ligand to an inactive phosphine oxide or phosphate form. However, catalysts in which the organic polymer additive is present in accordance with this invention can exhibit enhanced tolerance to oxygen under storage conditions.

The ratio of palladium to ligand is preferably sufficient to enhance catalyst stability but not unduly adversely affect its activity and/or selectivity. Frequently, the mole ratio of total ligand-forming compounds to palladium in the reaction menstruum is between about 0.1:1 and 100:1, say, between about 0.5:1 and 50:1, and preferably between about 1:1 to 20:1. The phosphorus-based ligand often comprises at least about 20 mole percent, e.g., about 30 mole percent to essentially all of the ligand-forming components in the reaction menstruum.

In preferred aspects of this invention, the atomic ratio of phosphorus from the phosphorus-based ligand and palladium is below about 5:1, say, between about 1.8:1 to 4.5:1, and most preferably, between about 2.0:1 to 4:1. At these lower phosphorus to palladium ratios, higher activity and selectivity to the alpha-substituted alkadiene are frequently obtained, and thus the advantages provided by the organic polymer additives can be better realized.

In accordance with this invention, the telomerization reaction is conducted in the presence of catalyst-stabilizing amounts of organic polymer additive. The polymer additive may be provided in conjunction with a separately prepared catalyst or provided directly to a catalyst-containing reaction menstruum. Often, the polymer additive is provided in an amount of at least about 0.1, e.g., about 0.5 to 500, say, about 5 to 100, parts by weight per part by weight of palladium contained in the catalyst. Excessive amounts of organic polymer additive are generally avoided to minimize any unduly adverse affect of the organic polymer additive on the activity of the catalyst.

The organic polymer additive is soluble in the reaction menstruum. For purposes herein, a polymer is considered to be soluble if it is dissolved or forms a stable colloidal suspension in the reaction menstruum. Advantageously, the solubility of the organic polymer additive in the reaction menstruum at 90° C. is at least about 0.5, preferably, at least about 1, gram per liter.

The functional groups of the organic polymer additives are preferably selected from the class consisting of amide (i.e. any

group regardless of further substitution), ketone, i.e., any

group regardless of further substitution), carbamates (i.e.

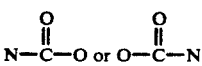

groups regardless of further substitution), urea (i.e., any

group regardless of further substitution) and carbonate (i.e.

group regardless of further substitution) groups.

Organic polymer additives include homopolymers, copolymers, terpolymers and oligomers containing such polar functional groups. The polar functional groups may be present in the organic polymer additives as radical substituents stemming off the backbone of the polymer and/or as groups that are incorporated in and form part of the backbone of the polymer. Further, said polar functional groups may be of a non-cyclic nature or part of a cyclic radical. The organic polymer additives may contain only one type of such polar functional groups or two or more different types of such polar functional groups. Illustrative organic polymers containing such polar functional groups include, e.g. polyvinylpyrrolidone and copolymers of vinylpyrrolidone (e.g., vinylpyrrolidone-vinyl acetate copolymers, copolymers of vinylpyrrolidone and long chain alpha olefins, copolymers of vinylpyrrolidone and styrene, and copolymers of vinylpyrrolidone and beta-dimethylaminoethyl methacrylate), polyvinylacetate and copolymers of vinyl acetate, polyacrylamides, carbamic acid, N-[polymethylene(polyphenyl)]-methylester, N-[polymethylene (polyphenyl)]N'-diisopropyl urea, polyacrylic acid hydrazide, poly-N-vinyl-5-methoxazolidone, polypeptides, e.g., poly-L-proline and poly-L-phenylalanine, polycaprolactone and copolymers thereof, and the like. The average molecular weight (weight average) of such organic polymers does not appear to be narrowly critical and may range from about 400 up to 10,000,000 or higher, nor does the amount of such polar functional groups on the polymer appear narrowly critical. The preferred organic polymer additives are those containing at least three such polar functional groups, especially functional amide groups, and more preferably vinylpyrrolidone polymers and copolymers. Vinylpyrrolidone-vinyl acetate copolymers because of their general superior solubility in many solvents are most preferred.

The reaction is conducted under telomerization conditions in a liquid solvent. Generally, because of expense, lower catalyst concentrations are desirable. This invention enables lower catalyst concentrations to be viable in light of the enhanced catalyst stability provided. Since less phosphorus-based ligand need be employed, desirable catalyst activity and selectivity can be achieved without undue sacrifice in catalyst stability. Often, the catalyst is present in a concentration of $1 \times 10^{-6}$ and lower, to 1 and higher, Molar in the reaction menstruum. Preferably, the Molar concentration of the palladium-containing catalyst is within the range of about $1 \times 10^{-4}$ to $1 \times 10^{-1}$.

The weight ratio of diolefin to total telomerization agent may also vary widely and is often between about 1000:1 to 0.1:1, say, about 100:1 to 0.5:1, and preferably between about 10:1 to 1:1. The amount of solvent used is, in part, a function of reaction conditions, the concentrations of the reactants and the properties of the solvent. In some instances, the telomerization agent may be in sufficient quantity to eliminate the need for a further solvent; however, the use of a solvent is generally desirable. Suitable solvents include aprotic polar organic solvents which are substantially inert under telomerization conditions. Preferably, the solvents are higher boiling than the reaction product to facilitate products recovery. Solvents include polyoxyalkylene glycol ethers, especially ethylene and propylene glycol ethers of 2 to 6 repeating units which are capped with lower alkyl, e.g., methyl or ethyl groups. Other solvents are dialkylsulfoxides such as dimethyl sulfoxide and sulfones such as sulfolane (tetrahydrothio-phene-1,1-dioxide), dioxane and acetonitrile.

In an aspect of this invention, the tendency of catalyst to crystallize during product recovery can be reduced by including in the solvent phase an effective amount of dialkylalkylene urea, e.g., dialkylethylene urea and dialkylpropyleneureas. Illustrative dialkylalkylene ureas are dimethylethylene urea, diethylethylene urea, di-n-propylethylene urea and methylethylethylene urea. The solvent may essentially comprise dialkylalkylene urea, or the dialkylalkylene urea may be present in an amount of at least about 5, say, about 10 to 90, volume percent or more of the total solvent. Generally, when employed, the dialkylalkylene urea is in an amount of at least about 1, say, about 3 to 90, volume percent of the reaction menstruum. An advantageous solvent composition comprises acetonitrile and dimethylethylene urea which, for instance, contains about 0.1 to 1.5 parts by volume of dimethylethylene urea per part by volume of acetonitrile. Advantageously, not only can the dialkylalkylene urea reduce the tendency of the catalyst to crystallize during product recovery, but also it often enhances the selectivity toward the alpha-substituted alkadiene.

The process may also be conducted using a solvent system having two liquid phases, one in which the catalyst is soluble and the other in which the catalyst is substantially insoluble, but the products are soluble, e.g., cyclohexane.

Additives may be used to enhance the process. Particularly useful additives include carbon dioxide, sulfur dioxide and/or carbonate anion. The carbon dioxide, sulfur dioxide and carbonate anion have been found to increase the rate of reaction. See, for instance, U.S. Pat. No. 3,992,456, column 2, lines 22 to 59, herein incorporated by reference. Carbon dioxide and/or sulfur dioxide and/or carbonate anion may advantageously be present in the reaction mixture in an amount sufficient to enhance the rate of reaction, e.g., often at least about 0.0001, preferably, between about 0.001 and 1, say, 0.01 to 0.5, mole per mole of diolefin. Another class of additives that have been proposed are the triorganophosphine oxides. See, for instance, European Patent Application 411,410, herein incorporated by reference.

U.S. Pat. No. 4,962,243 proposes the use of strong non-coordinating acids to enhance the yields of desired products. Non-coordinating acids include tetrafluoroboric acid, methanesulfonic acid, trifluoromethane sulfonic acid and the like. When used, the molar ratio of acid to palladium is generally in the range of 0.001:1 to 1.5:1. Japanese patent application Kokai 53/147013 proposes the use of solid acids having an acid strength no greater than zero such as zirconium monohydrogen phosphate and aluminum phosphate to enhance the yield of telomerization product. Japanese patent application Kokai 62/15538 discloses the use of oxide co-catalysts to enhance selectivity. These catalysts contain boron, indium, germanium, tin, tellurium, titanium, zirconium, niobium, molybdenum or tungsten.

The reaction is usually carried out under elevated temperature and pressure. At lower temperatures, the reaction may not proceed sufficiently rapidly to provide a commercially attractive process and at higher temperatures, catalyst decomposition and/or loss of selectivity to the desired product may occur. Often, the reaction temperature is between about 30° C. and 150° C., say, between about 50° C. and 150° C., and the pressure is within the range of about 1.1 to 50, say, 5 to 25, bar absolute.

The process may be conducted in the batch, semicontinuous or, preferably, continuous mode. The reactor may be of any convenient configuration, e.g., tubular reactors and, more preferably, stirred tank reactors. The duration of the telomerization reaction may vary widely depending upon the other reaction conditions and the desired conversion. The reaction may be conducted until the reactants (e.g., conjugated diolefin) are substantially consumed. However, frequently, the conversion of conjugated diolefin is between about 20 or less to 95 or 98 or more percent. If the conversion is too low, recovery and recycling unreacted diolefin, which may be essential to achieving a viable process, may prove to be too costly for commercial purposes. At higher conversions, the desired products may be more likely to be further consumed, e.g., by isomerization, degradation, or dehydration, to produce unwanted products. For instance, octadien-1-ol can, at elevated temperatures and in the presence of telomerization catalyst, be consumed to product octatriene. Often, the residence time in the reaction zone is at least about 0.01 to 20 or more, e.g., about 0.05 to 5, hours.

The reaction zone product typically contains the desired telomerization product, starting materials, catalyst, additives and solvent. The telomerization product can be recovered by any suitable means and at least a portion of the remaining material, which includes the palladium-containing catalyst, is preferably recycled to the reaction zone. Separation mechanisms include distillation (e.g., thin film evaporators and vacuum distillation) and extraction. Extraction, for instance, can be accomplished using an organic liquid in which the catalyst and telomerizing agent have little, if any, solubility. Such extracting liquids include aliphatic and alicyclic hydrocarbons such as n-butane, isobutane, butene, isobutene, n-pentane, n-hexane, cyclohexane, cyclohexene, methyl cyclohexane, n-octane, isooctane, etc., and mixtures thereof. The extractant layer can be subjected to distillation to isolate the desired product. See, for instance, U.S. Pat. No. 4,417,079, column 8, line 33, to column 10, line 46, herein incorporated by reference. Catalyst separation may be accomplished by ultrafiltration.

The product includes alpha-substituted telomerization product. As stated above, the alpha substituent will depend upon the telomerization agent. With water, the product comprises alkadien-1-ol. With, e.g., an alcohol, the product is an alkoxide. The substituted product may be hydrogenated under suitable hydrogenation conditions to produce a substituted, saturated alkane. Typical hydrogenation catalysts include supported palladium, supported platinum, supported rhodium, Raney nickel, Raney cobalt, modified Raney nickel, supported nickel and supported ruthenium. Hydrogenation temperatures usually range from about 25° C. to 200° C., Preferably, 50° C. to 150° C., and a hydrogen pressure of about 1 to 200 bar absolute is often used. The hydrogenation may be conducted in a liquid menstruum, e.g., using an inert organic solvent such as cyclohexane, n-hexane, n-butanol, n-hexanol, dimethylethylene urea, tetrahydrofuran, etc.

The following examples are provided to further illustrate the invention but are not in limitation thereof. All parts and percentages of solids and liquids are by weight and of gases are by volume unless otherwise noted or clear from the context.

EXAMPLE 1

Comparative

A glass Fischer-Porter pressure reaction vessel is charged with palladium acetylacetonate (0.186 g, 0.6 mmol) and triphenylphosphine (0.818 g, 3.1 mmol). The vessel is sealed, purged with nitrogen and then 22 milliliters of acetonitrile are added. About 2.8 milliliters of water are added via syringe. The vessel is pressurized to about 6.5 bar absolute with $C_2$, and butadiene (8.8 milliliters, 97.8 mmol) is added via syringe. The solution is heated to 90° C. with magnetic stir bar stirring for 6 hours.

A sample of the reaction mixture is analyzed by gas chromatography and the analysis shows that 98% butadiene is converted with telomerization products consisting of 51 wt. % octa-2,7-dien-1-ol, 20 wt. % octa-1,7-dien-3-ol, 29 wt. % octatriene (excluding heavy products).

The remaining reaction mixture in the reaction vessel is heated at 90° C. for a total of 13 hours before catalyst decomposition, characterized by deposition of a palladium mirror, is observed.

EXAMPLE 2

A reaction mixture substantially identical to that of Example 1, except containing 10 milligrams of polyvinylpyrrolidone having a reported average molecular weight of about 10,000, available as PVP-K15 (GAF Corp.), per milligram of palladium acetylacetonate, is prepared and heated to 90° C. for a total of 22 hours before deposition of a palladium mirror is observed. The telomerization products produced consist of 65 wt. % octa-2,7-dien-1-ol, 19 wt. % octa-1,7-dien-3-ol, and 16 wt. % octatriene (excluding heavy products) as determined by gas chromotography.

Examples 1 and 2 illustrate the extended lifetime at 90° C. of a catalyst containing 5 moles of phosphorus-based ligand per mole of palladium by addition of polyvinylpyrrolidone.

A reaction mixture containing palladium acetylacetonate (0.184 g, 0.6 mmol), triphenylphosphine (0.624 g, 2.4 mmol), 22 milliliters of acetonitrile, 3.6 milliliters of water, 8.8 milliliters of butadiene, and a polyvinyl pyrrolidone/vinyl acetate (60:40 mole ratio) copolymer having a number average molecular weight of about 12400 (available as PVP-VA from GAF Corp.) present in a ratio of 10 milligrams of copolymer per milligram of palladium acetylacetonate, is heated to 75° C. under about 6.5 bar absolute $CO_2$ for 4 hours. Analysis by gas chromatography reveals 50% butadiene conversion with the telomerization products containing 76 wt. % octa-2,7-dien-1-ol, 7 wt. % octa-1,7-dien-3-ol, 6 wt. % octatriene, and 3 wt. % bis(octadienyl)ethers.

EXAMPLE 4

Comparative

A reaction mixture containing 0.184 grams of palladium acetylacetonate (0.6 mmol), 0.627 grams triphenylphosphine (2.4 mmol), 22 milliliters of acetonitrile, 3.6 milliliters of water, and 7.7 milliliters of butadiene is prepared and heated under 6.5 bar absolute $CO_2$ at 100° C. for 5 hours before deposition of a palladium mirror is observed.

EXAMPLE 5

A catalyst solution containing 0.091 grams of palladium acetylacetonate (0.3 mmol), 0.31 grams of triphenylphosphine (1.2 mmol), 12 milliliters acetonitrile, 2.7 milliliters of water, 4.4 milliliters butadiene and polyvinylpyrrolidone (PVP-K15) present in a weight ratio of 5 milligrams of copolymer per milligram of palladium acetylacetonate, is heated under about 6.5 bars absolute of $CO_2$ at 100° C. for 12 hours before deposition of a palladium mirror is observed.

Examples 4 and 5 illustrate the extended lifetime at 100° C. of a catalyst consisting of 4 moles of phosphorus-based ligand per mole of palladium by addition of organic polymer additive.

EXAMPLE 6

A catalyst solution substantially identical to that of Example 4, but containing the polyvinylpyrrolidone in a ratio of 10 milligrams per milligram of palladium acetylacetonate is heated at 75° C. for 2 hours under about 6.5 bars absolute $CO_2$. Analysis of the reaction products by gas chromatography reveals 86% butadiene conversion with telomerization products comprising 85 wt. % octa-2,7-dien-1-ol, 8 wt. % octa-1,7-dien-3-ol, and 7 wt. % octatriene (excluding heavy products). The mixture is then heated at 100° C. for 60 hours without observing deposition of a palladium mirror.

Examples 4 and 6 illustrate the extended lifetime at 100° C. of a catalyst composed of 4 moles of phosphorus-based ligand/mol palladium by addition of polyvinylpyrrolidone.

Examples 2 and 6 also demonstrate that in the presence of organic polymer additive, the ligand/palladium ratio of the catalyst can be decreased, resulting in better selectivity to the desired octa-2,7-dien-1-ol product, without sacrificing catalyst stability at high temperatures.

EXAMPLE 7

A catalyst solution substantially identical to that in Example 5, but containing polyvinylpyrrolidone (PVP-K15) in a weight ratio of 15 milligrams of polymer per milligram of palladium acetylacetonate, is heated under about 6.5 bars absolute $CO_2$ at 100° C. for 72 hours before deposition of a palladium mirror is observed.

Examples 4 through 7 illustrate that for a given concentration of palladium, increasing amounts of polyvinylpyrrolidone increase the catalyst lifetime. However, the increase in lifetime appears to diminish at higher concentrations.

EXAMPLES 8 TO 26

The following reactions are conducted in Fischer-Porter reactors under about 8 atmospheres absolute of carbon dioxide. Palladium acetylacetonate, triphenyl phosphine and, if used, Polyvinylpyrrolidone (PVP-K15) are charged to the reactor before sealing. The reactor is then evacuated and placed under an inert atmosphere (nitrogen or argon). Solvent, water and butadiene are added through a septum inlet to the reactor. The reactor is then pressurized and placed in an oil bath at the sought temperature.

Samples are periodically withdrawn from the reactor by pressure lock syringes, placed in sample vials and cooled in an ice bath to stop the reaction.

The reaction products, at the completion of the batch reaction, can be separated from the catalyst using a falling film evaporator at 100° C. and about 0.03 atmosphere absolute.

The following standard conditions are used for the following examples:

| Solvent | 22 milliliters |
| Butadiene | 9 milliliters |
| Palladium acetylacetonate | 0.18 grams |

A summary of the examples is provided in Table I.

TABLE I

| Example | Solvent | P/Pd (Atomic) | H2O/BD (mole) | T, °C. | Conversion, 90 min | Selectivity, Wt. % | | | |
|---|---|---|---|---|---|---|---|---|---|
| | | | | | | octatriene | 3-ol | 1-ol | ethers |
| 8[e] | A[a] | 5 | 1 | 90 | 69% | 9 | 11 | 63 | 2 |
| 9[e] | A | 5 | 5 | 90 | 26% | 22 | 3 | 50 | — |
| 10[e] | A | 5 | 1 | 75 | 53% | 9 | 11 | 62 | 3 |
| 11[e] | A | 5 | 0.5 | 90 | 89% | 39 | 17 | 16 | 2 |
| 12[e] | A | 5 | 2 | 90 | 95% | 9 | 13 | 59 | 5 |
| 13[e] | A | 4 | 2 | 75 | 81% | 8 | 5 | 76 | 1 |
| 14[e] | A | 4 | 1 | 75 | 75% | 14 | 14 | 54 | 4 |
| 15[a, e] | A | 4 | 2 | 75 | 54% | 12 | 6 | 70 | 1 |

TABLE I-continued

| Example | Solvent | P/Pd (Atomic) | H$_2$O/BD (mole) | T, °C. | Conversion, 90 min | Selectivity, Wt. % | | | |
|---|---|---|---|---|---|---|---|---|---|
| | | | | | | octatriene | 3-ol | 1-ol | ethers |
| 16[e] | A | 4 | 2 | 75 | 78% | 8 | 6 | 73 | 4 |
| 17[e] | B[b] | 4 | 2 | 75 | 69% | 8 | 9 | 76 | 2 |
| 18[c, e] | A | 4 | 2 | 75 | 35% | 11 | 5 | 62 | 4 |
| 19[d, e] | A | 4 | 2 | 75 | ~50% | 9 | 8 | 58 | 15 |
| 20[e] | C[h] | 4 | 2 | 75 | 81% | 17 | 19 | 50 | — |
| 21[e, f] | C | 4 | 2 | 75 | 81% | 12 | 14 | 57 | — |
| 22 | C | 4 | 2 | 75 | 94% | 14 | 23 | 57 | 1 |
| 23 | C | 3 | 3 | 65 | 97% | 4 | 13 | 76 | 3 |
| 24[e] | C | 3 | 3 | 65 | 83% | 8 | 15 | 70 | 1 |
| 25[g] | C | 2 | 3 | 65 | 99% | 6 | 11 | 72 | 7 |
| 26 | C | 3 | 3 | 65 | 83% | 8 | 8 | 70 | 6 |

[a]Solvent: Acetonitrile
[b]Solvent: 3:1 CH$_3$CN/DMEU
[c][Pd] = .01M
[d]1 mole solvent per mole butadiene
[e]Containing PVP, 10 milligrams per milligram palladium acetylacetonate
[f]Catalyst is recovered from Example 20
[g]Catalyst decomposition occurs
[h]Solvent: Dimethylethylene urea

EXAMPLE 27

A reaction menstruum containing 0.091 gram of palladium acetylacetonate (0.3 mmol), 0.32 gram of triphenylphosphine (1.2 mmol), 11 milliliters dimethylethylene urea, 1.8 milliliters of water, 3.8 milliliters of butadiene and polyvinylacetate present in a weight ratio of 10 milligrams of polymer per milligram of palladium acetylacetonate, is heated under about 6.5 bars absolute of CO$_2$ at 100° C. for 52 hours before deposition of a palladium mirror is observed. Octadienols are produced.

EXAMPLE 28

A reaction menstruum substantially identical to that of example 27, but containing polycaprolactone instead of polyvinylacetate in a weight ratio of 10 milligrams of polymer per milligram of palladium acetylacetonate, is heated under about 6.5 bars absolute of CO$_2$ at 100° C. for 66 hours without the deposition of a palladium mirror. Octadienols are produced.

EXAMPLE 29

Comparative

A reaction menstruum containing 0.034 gram of palladium acetylacetonate (0.1 mmol), 0.089 gram of triphenylphosphine (0.3 mmol), 8 milliliters of dimethylethylene urea, 8 milliliters triethylamine, 2 milliliters of butadiene (22 mmol), and 3.813 grams of crotonic acid (44 mmol) is heated at 75° C. under nitrogen for 2 hours. Analysis of the reaction mixture by gas chromatography reveals 81% butadiene conversion with telomerization products comprising 69% octadienyl crotonates and 21% octatrienes. The mixture is then heated at 100° C. for 26 hours before deposition of a palladium mirror is observed.

EXAMPLE 30

A reaction menstruum containing 0.034 gram palladium acetylacetonate (0.1 mmol), 0.089 gram triphenylphosphine (0.3 mmol), 16 milliliters dimethylethylene urea, 2 milliliters of butadiene (22 mmol), 3.81 grams of crotonic acid (44 mmol) and polyvinylpyrrolidone (PVP-K15) present in a weight ratio of 10 milligrams per milligram of palladium acetylacetonate, is heated at 75° C. under nitrogen for 2 hours. Analysis of the reaction mixture by gas chromatography reveals 85% butadiene conversion with telomerization products comprising 33% octatrienes and 66% octadienyl crotonates. The mixture is then heated at 100° C. for 62 hours before the deposition of a palladium mirror is observed.

Examples 29 and 30 demonstrate the superiority of organic polymer additive over amine additive in the telomerization process.

EXAMPLE 31

Comparative

A reaction menstruum containing 0.092 gram of palladium acetylacetonate (0.3 mmol), 0.324 gram triphenylphosphine (1.2 mmol), 11 milliliters of acetonitrile, 1.8 milliliters of water, 3.8 milliliters of butadiene, and 2,2'-bipyridyl present in a weight ratio of 10 milligrams bipyridyl per milligram of palladium acetylacetonate is heated under about 6.5 bar absolute of CO$_2$ at 100° C. for 14 hours before deposition of a palladium mirror is observed. Octadienols are produced.

Examples 6 and 31 illustrate the superiority of organic polymer additive over amine additive in the telomerization process.

EXAMPLE 32

Comparative

A reaction menstruum containing 0.09 gram of palladium acetylacetonate (0.3 mmol), 0.32 gram of triphenylphosphine (1.2 mmol), 11 milliliters acetonotrile, 1.8 milliliters of water, and 1.8 milliliters of butadiene, and containing 0.063 gram of succinimide (0.6 mmol) is heated to 100° C. under about 6.5 bar absolute of CO$_2$ for 15 hours before deposition of a palladium mirror is observed. Octadienols are produced.

Examples 6 and 32 illustrate the superiority of organic polymer additive over succinimide in the telomerization process.

We claim:

1. In a process for the telomerization of conjugated diolefin with an active hydrogen-containing telomerization agent in a solvent-containing liquid menstruum under telomerization conditions including the presence of palladium-containing telomerization catalyst which is comprised of a complex of palladium or palladium compound and phosphorus-based ligand, an improvement wherein the solvent comprises dialkylalkylene urea.

2. The process of claim 1 in which the dialkylalkylene urea is dialkylethylene urea.

3. In a process for the telomerization of conjugated diolefin with an active hydrogen-containing telomerization agent in a solvent-containing liquid menstruum under telomerization conditions including the presence of palladium-containing telomerization catalyst which is comprised of a complex of palladium compound and phosphorus-based ligand to produce substituted alkadiene comprising alpha-substituted alkadiene, an improvement wherein the liquid menstruum comprises dialkylalkylene urea in an amount sufficient to enhance the selectivity of the alpha-substituted alkadiene.

4. The process of claim 3 in which the conjugated diolefin comprises butadiene, the telomerization agent comprises water and the alpha-substituted diolefin is octadien-1-ol.

5. The process of claim 3 in which the dialkylalkylene urea comprises dialkylethylene urea.

6. The process of claim 5 in which the dialkylethylene urea comprises dimethylethylene urea.

* * * * *